United States Patent
Becker et al.

(10) Patent No.: US 6,652,568 B1
(45) Date of Patent: Nov. 25, 2003

(54) RADIOPAQUE BALLOON

(75) Inventors: Jon A. Becker, Danville, CA (US); Christopher C. Pfaff, Palo Alto, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/469,414

(22) Filed: Dec. 22, 1999

(51) Int. Cl.⁷ .................. A61M 29/00; A61M 31/00; A61F 2/06
(52) U.S. Cl. ............... 623/1.11; 604/96.01; 604/103.1; 623/1.2
(58) Field of Search .................... 600/434, 3, 588; 606/41, 192–198, 108; 604/913, 96, 108, 103.14, 103.01, 103.1, 164.01, 509, 96.01

(56) References Cited

U.S. PATENT DOCUMENTS

| | | | |
|---|---|---|---|
| 4,364,392 A | * 12/1982 | Strother et al. | 606/195 |
| 4,846,174 A | * 7/1989 | Willard et al. | 604/913 |
| 4,946,464 A | * 8/1990 | Pevsner | 264/308 |
| 4,952,357 A | 8/1990 | Euteneuer | 264/129 |
| 4,990,138 A | 2/1991 | Bacich et al. | 604/96 |
| 4,994,032 A | 2/1991 | Sugiyama et al. | 604/96 |
| 5,141,494 A | * 8/1992 | Danforth et al. | 600/434 |
| 5,201,754 A | 4/1993 | Crittenden et al. | 606/194 |
| 5,209,730 A | 5/1993 | Sullivan | 604/96 |
| 5,259,837 A | 11/1993 | Van Wormer | 604/96 |
| 5,312,340 A | 5/1994 | Keith | 604/96 |
| 5,669,879 A | 9/1997 | Duer | 604/96 |
| 5,752,934 A | 5/1998 | Campbell et al. | |
| 5,759,174 A | * 6/1998 | Fischell et al. | 604/103.1 |
| 5,868,704 A | 2/1999 | Campbell et al. | |
| 5,947,889 A | * 9/1999 | Hehrlein | 600/3 |
| 6,010,511 A | * 1/2000 | Murphy | 606/108 |
| 6,027,510 A | * 2/2000 | Alt | 606/108 |
| 6,120,477 A | 9/2000 | Campbell et al. | |
| 6,254,599 B1 | * 7/2001 | Lesh et al. | 606/141 |
| 6,428,506 B1 | 8/2002 | Simhambhatla et al. | |

* cited by examiner

Primary Examiner—Brian L. Casler
Assistant Examiner—Roz Ghafoorian
(74) Attorney, Agent, or Firm—Fulwider Patton Lee & Utecht, LLP

(57) ABSTRACT

The present invention is directed to a balloon for an intracorporeal catheter having at least a portion of its walls having radiopaque properties. The balloon is formed of a polymeric material, which has a single wall thickness of at about 0.001 inches to about 0.0125 inches while deflated. The radiopaque portion of the balloon has a thickness of about 0.00025 inches to about 0.012 inches, specifically about 0.002 inches to about 0.003 inches. The balloon is constructed of layers. The radiopaque material may be embedded within the film or deposited on the film to create radiopaque properties.

26 Claims, 3 Drawing Sheets

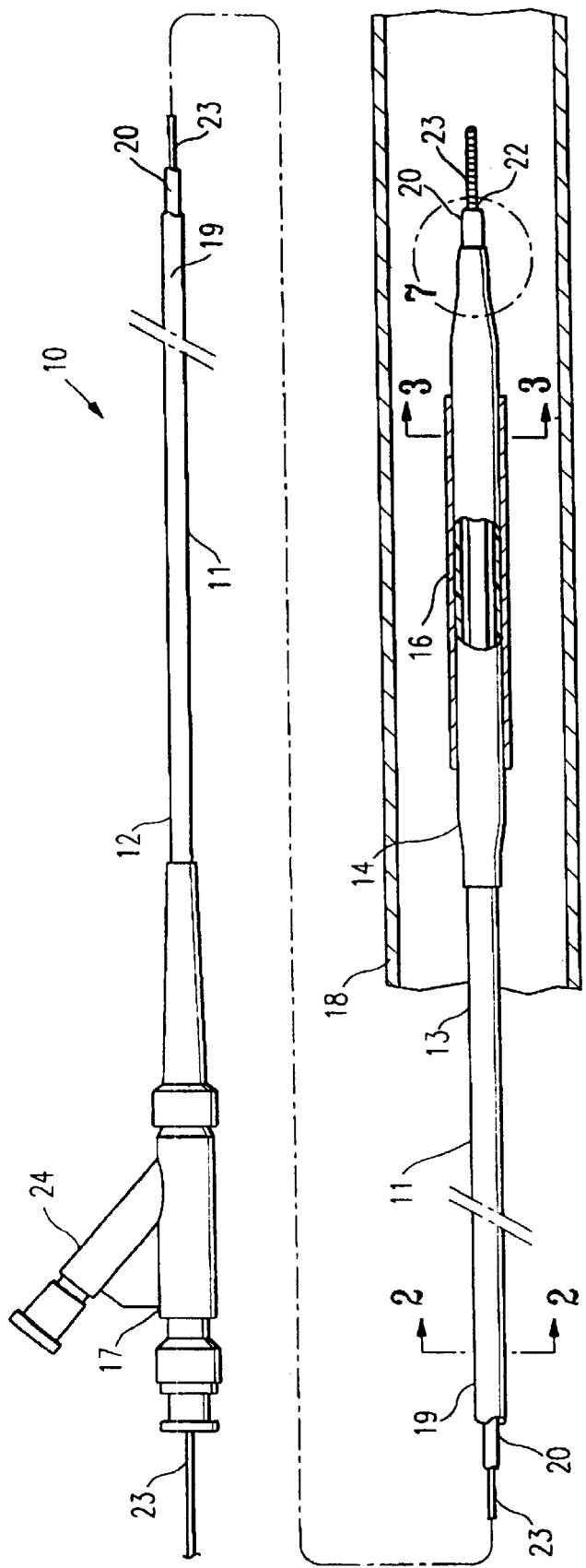
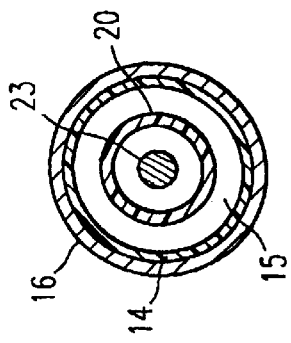
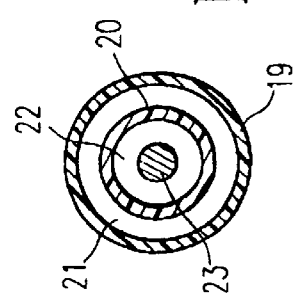
FIG. 1
FIG. 2
FIG. 3

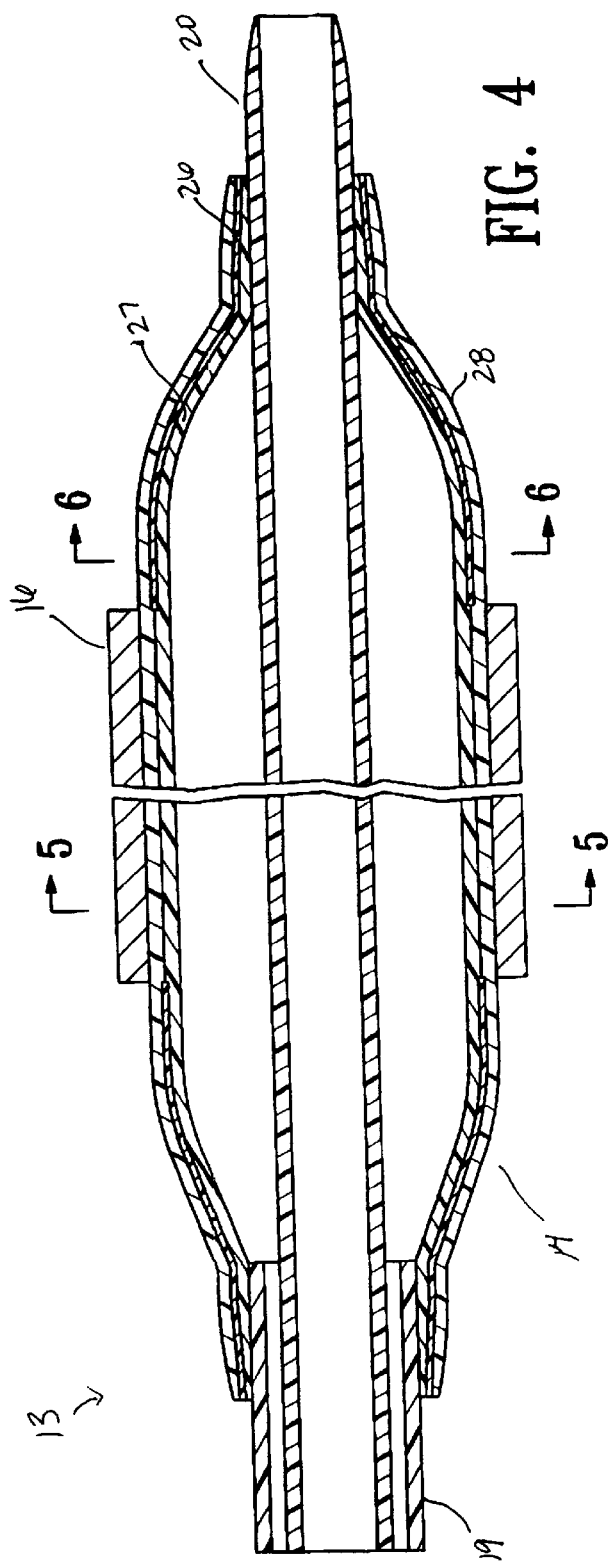
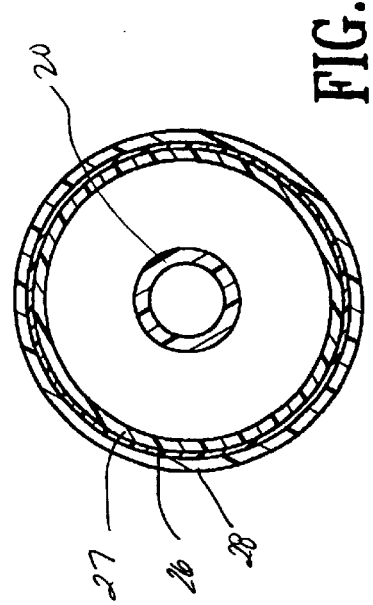
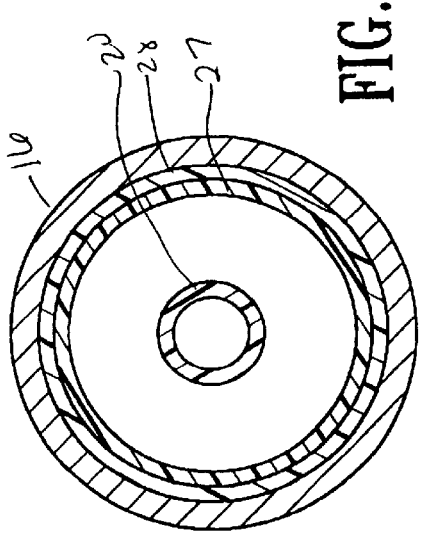

RADIOPAQUE BALLOON

BACKGROUND OF THE INVENTION

This invention generally relates to the field of intravascular balloon catheters, and more particularly to a balloon catheter with a radiopaque balloon.

Percutaneous transluminal coronary angioplasty (PTCA) is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow there through.

To facilitate the advancement of the dilatation catheter into the patient's coronary artery, a guiding catheter having a preshaped distal tip is first percutaneously introduced into the cardiovascular system of a patient, using the Seldinger technique, through the brachial or femoral arteries. The catheter is advanced until the preshaped distal tip of the guiding catheter is disposed within the aorta adjacent the ostium of the desired coronary artery. The distal tip of the guiding catheter is then maneuvered into the ostium. A balloon dilatation catheter may then be advanced through the guiding catheter into the patient's coronary artery until the balloon on the catheter is disposed within the stenotic region of the patient's artery. The balloon is inflated to open up the arterial passageway and increase the blood flow through the artery.

The physician uses fluoroscopy to observe the balloon and properly place it within the stenosis. The catheter shaft generally has radiopaque markers on its inner member within the balloon, so the placement of the balloon can be determined before inflation. In spite of this, the precise location of the balloon frequently cannot be reliably determined by using the radiopaque markers alone.

After placement, the operator will inject radiopaque materials, such as Renograffin, into the inflation lumen to inflate the balloon. The radiopaque material allows the operator to view the inflation of the balloon. However, such radiopaque materials are expensive, and the viscosity is high so that inflation and deflation times are slow compared to saline solution.

Generally, the inflated diameter of the balloon is approximately the same diameter as the native diameter of the body lumen being dilated so as to complete the dilatation but not over expand to the point of damaging the artery wall. After the balloon is finally deflated, blood flow resumes through the dilated artery and the dilatation catheter can be removed therefrom.

In a large number of angioplasty procedures, there may be a restenosis, i.e. reformation of the arterial plaque. To reduce the restenosis rate and to strengthen the dilated area, physicians now frequently implant an intravascular prosthesis called a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent is left in place within the artery at the site of the dilated lesion. See for example, U.S. Pat. No. 5,507,768 (Lau et al.) and U.S. Pat. No. 5,458,615 (Klemm et al.), which are incorporated herein by reference.

However, extremely flexible balloons lack support when the balloon is maneuvered through a stenosis. First, the balloon has a tendency to bend easily in the transition areas, which are the areas proximal and distal to the stent placement. Second, the balloon may fold back on itself in the transition areas when force is applied longitudinally to attempt to cross a stenosis. Both cases cause reduced access and cross ability, making proper placement within the stenosis more difficult.

If the balloon is not properly placed during a dilatation, and especially during a stenting procedure, the inflation of the balloon and stent against the vessel wall may cause damage to the non-stenosed tissue. Proper placement is difficult because the balloon itself is not generally radiopaque, so the operator does not have the precise location of the balloon, the working length and the stent. Radiopaque markers on the inner member of the catheter shaft aid in stent placement but the location of the markers are not a guarantee of the location of the balloon and the stent within the stenosis.

Therefore, what has been needed is a balloon catheter with improved radiopaque properties to improve placement and visibility of the balloon. Additionally, a balloon catheter with improved stiffness, especially in the transition areas, has also been needed to improve cross ability. The present invention satisfies these and other needs.

SUMMARY OF THE INVENTION

The present invention is directed to a balloon for an intracorporeal catheter with at least a portion of its walls having radiopaque properties. The balloon is formed of a polymeric material, which has a deflated single wall thickness of at least 0.001 inches to about 0.0125 inches, preferably about 0.005 inches to about 0.012 inches.

The thickness of the balloon wall allows for a substantial amount of radiopaque material to be doped into the walls, creating a truly radiopaque balloon. In thinner wall balloons, adding enough radiopaque material to make the balloon easily visible will change the properties of the balloon. The radiopaque layer is about 0.00025 inches to about 0.012 inches for sufficient radiopacity without changing the properties of the balloon. Specifically, the radiopaque layer is about 0.002 inches to about 0.003 inches. The thick walls additionally allow for addition of other materials to enhance any properties of the balloon.

The balloon is formed of a polymer material. Specifically, polymers creating balloons having a thicker wall when deflated, and a thinner wall when inflated, are available for this invention. These types of balloons are known as formed in place balloons because they are generally formed during dilatation at the desired location, as opposed being preformed, then wrapped about the catheter shaft before entry and unwrapped upon dilatation.

More specifically, the balloon is preferably formed of porous expanded polytetrafluoroethylene. Examples of porous expanded polytetrafluoroethylene are described in U.S. Pat. No. 3,953,566 (Gore), U.S. Pat. No. 4,187,390 (Gore) and U.S. Pat. No. 5,753,358 (Korleski), all assigned to W. L. Gore and Associates, Inc., which are incorporated herein by reference. An additional preferred polymer material is ultra high molecular weight polyethylene. However, any polymer that creates a balloon having walls with a deflated minimum thickness of 0.001 inches would be suitable for the radiopaque balloon of this invention.

The present invention is also preferably constructed with layers to allow control over the eventual radiopaque properties of the finished balloon. Balloons can be constructed in layers by many methods known in the art. These methods include, but are not limited to, wrapping the balloon material about a mandrel, dipping a mandrel into a polymeric dispersion, and sputtering the polymeric dispersion on to a mandrel. The method using layers gives control over the process so that the radiopaque material can be either layered or combined with the balloon material in specific designs and at specific locations.

The radiopaque portion may be either doped into the polymeric material at a loading percentage of about 70% to about 90%, or deposited on the outer wall, the inner wall, or between layers of the balloon. The radiopaque material could be located on all or part of the balloon. The placement of the radiopaque material can make any shape on the balloon, including but not limited to diamonds, circles, rings and stripes. Any design, shape or placement of the radiopaque material is available because of the controlled manufacture. For both embodiments, the layer containing the radiopaque material is about 0.00025 inches to about 0.012 inches, preferably 0.002 inches to about 0.003 inches.

Another embodiment of the invention includes elastomeric or inelastic material combined within the balloon or as a layer adjacent to the balloon. Such embodiments could combine the properties of known balloons with the radiopaque properties available in this invention. Such properties include, but are not limited to, better inflation and deflation characteristics.

The balloon of this invention provides for improved radiopaque properties in the balloon. Additionally, the balloon's layered manufacturing allows for specific placement of the radiopaque materials. These and other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter, which embodies features of the invention, showing a balloon in a partially expanded state.

FIG. 2 is a transverse cross sectional view of the catheter of FIG. 1 taken along lines 2—2.

FIG. 3 is a transverse cross sectional view of the catheter of FIG. 1 taken along lines 3—3.

FIG. 4 is an enlarged longitudinal cross sectional view of a balloon embodying features of the invention.

FIG. 5 is a transverse cross sectional view of the balloon of FIG. 4 taken along line 5—5.

FIG. 6 is a transverse cross sectional view of the balloon of FIG. 4 taken along line 6—6.

DETAILED DESCRIPTION OF THE INVENTION

Figure 7:
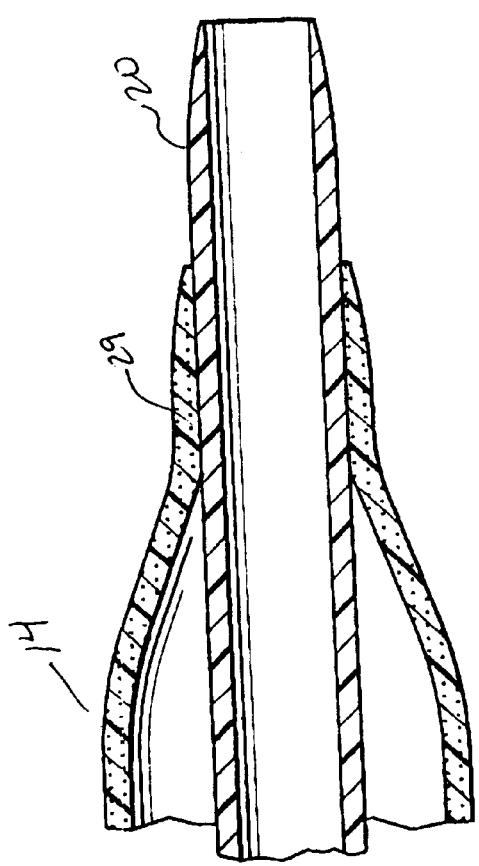
FIG. 7 is an enlarged longitudinal cross sectional view of the catheter shown in FIG. 1 taken within circle 7.

As shown in FIGS. 1–3, the catheter 10 of the invention generally includes an elongated catheter shaft 11 having a proximal section 12 and a distal section 13, an inflatable balloon 14 having a radiopaque wall section on the distal section 13 of the catheter shaft 11, ad an adapter 17 mounted on the proximal section 12 of shaft 11 to direct inflation fluid to the interior of the inflatable balloon 14. Balloon 14 is a formed in place balloon, specifically constructed with layers of polymeric material. The embodiment shown in FIG. 1 includes a stent 16 disposed about the balloon 14.

In the embodiment illustrated in FIG. 1, the intravascular catheter 10 of the invention is an over-the-wire catheter and is illustrated within a patient's body lumen 18, with the balloon 14 in a partially expanded state. The catheter shaft 11 has an outer tubular member 19 and an inner tubular member 20 disposed within the outer tubular member 19 and defining, with the outer tubular member 19, annular inflation lumen 21. Inflation lumen 21 is in fluid communication with the interior chamber 15 of the inflatable balloon 14. The inner tubular member 20 has an inner lumen 22 extending therein, which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon 14 is sealingly secured to the distal extremity of the outer tubular member 19. Balloon 14 is formed of a polymeric material, specifically porous expanded polytetrafluoroethylene or ultra high molecular weight polyethylene. The deflated single tall thickness is at least about 0.001 inches to about 0.0125 inches.

At least a portion of balloon 14 is radiopaque. FIGS. 4–6 illustrate one embodiment of the invention having a radiopaque layer 26 between two layers of the balloon 14. The radiopaque layer 26 may be deposited either on the outer wall of the bottom layer 27, or on the inner wall of the upper layer 28. In the embodiment illustrated in FIG. 4, the radiopaque layer 26 extends from the proximal end of the balloon 14 to the proximal end of the stent 16, and then from the distal end of the stent 16 to the distal end of the balloon 14. This embodiment would show the exact location of the stent during placement. Additionally, this embodiment may increase stiffness in the transition regions.

Figure 8:
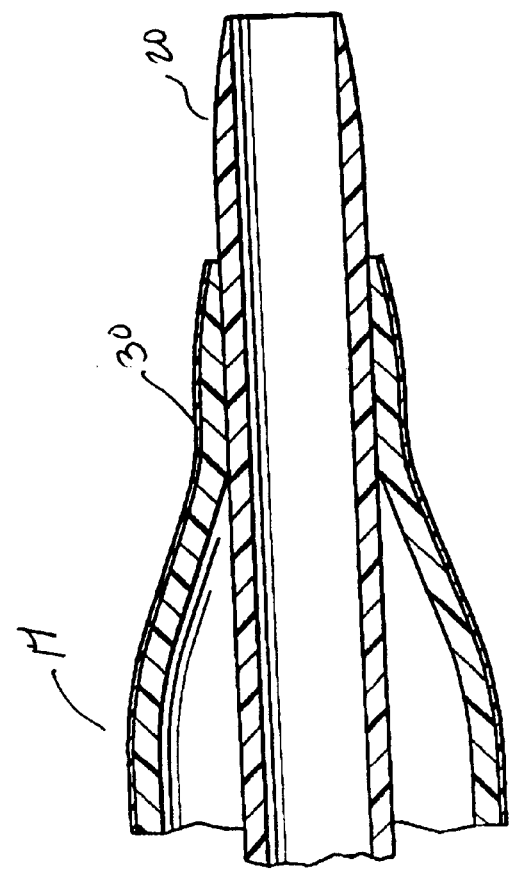
FIG. 8 is a longitudinal cross sectional view of an additional embodiment of the catheter shown in FIG. 1 taken within circle 7.

FIGS. 7 and 8 depict additional embodiments of the radiopaque portion. FIG. 7 shows the radiopaque material 29 doped into the balloon material. This may be accomplished by placing the radiopaque material into the polymeric material before balloon construction. The loading percentage of radiopaque material within the polymeric material will be about 70% to about 90% by weight. Specifically, the loading percentage is about 80% to about 85%. FIG. 8 shows the radiopaque material 30 deposited on to the outer wall of the balloon 14. The radiopaque material 30 may also be deposited on the inner wall of the balloon 14. Radiopaque materials suitable for this invention include, but are not limited to, barium, bismuth, tungsten, iridium, iodine, gold, iron, or platinum. Specifically, tungsten, iridium, gold and platinum are suitable and create a sufficiently radiopaque layer. The radiopaque layer will be about 0.00025 inches to about 0.012 inches, preferably about 0.002 inches to about 0.003 inches.

The material may be placed at any location along the balloon, and in any design, depending on the desired characteristics of the balloon. Therefore, the balloon could have radial rings of radiopaque material at predetermined locations along the longitudinal axis of the balloon 14 (not shown). The balloon could also have longitudinal stripes of radiopaque material along the entire length, or the working length of the balloon 14 (not shown). The entire balloon 14 could be radiopaque. A preferred embodiment would have at least the ends of the working length and the ends of the stent marked with radiopaque material, similar to the embodiment illustrated in FIG. 4.

Additional embodiments of balloon 14 may include an elastomeric layer or an inelastic layer to aid in deflation and other balloon properties (not shown). The elastomeric and inelastic material may alternatively be imbedded within the balloon material (not shown). The embodiments help control inflation and aid in deflation of the balloon.

Although individual features of embodiments of the invention may be shown in some of the drawings and not in others, those skilled in the art will recognize that individual features of one embodiment of the invention can be combined with any or all the features of another embodiment.

What is claimed is:

1. A catheter balloon, comprising a polymeric wall which extends from and defines an outer surface and an inner surface of the balloon, and which is configured to retain inflation fluid in an interior of the balloon, and which has at least a layer formed of a porous polymeric material, and which has a deflated single wall thickness of at least 0.001 inches to about 0.0125 inches, and the balloon having radiopaque material within the polymeric wall, the radiopaque material extending along at least a section of a layer to form a radiopaque section of the balloon.

2. The balloon of claim 1 wherein the radiopaque section has a thickness of about 0.00025 inches to about 0.012 inches.

3. The balloon of claim 1 wherein the radiopaque section has a thickness of about 0.002 inches to about 0.003 inches.

4. The balloon of claim 1 wherein the balloon is formed of porous expanded polytetrafluoroethylene.

5. The balloon of claim 1 wherein the balloon is formed of ultra high molecular weight polyethylene.

6. The balloon of claim 1 wherein the balloon is formed of at least two layers of polymeric material.

7. The balloon of claim 1 including radiopaque material on an outer surface.

8. The balloon of claim 6 wherein the radiopaque material is between the two layers of the polymeric material.

9. The balloon of claim 1 wherein the radiopaque material is within a polymeric layer of the wall.

10. The balloon of claim 1 wherein the entire length of the balloon is radiopaque.

11. The balloon of claim 1 having radiopaque sections and non-radiopaque sections.

12. The balloon of claim 1 wherein the radiopaque material is in the shape of at least one radial ring.

13. The balloon of claim 1 wherein the radiopaque material is in the shape of at least one longitudinal radiopaque stripe.

14. The balloon of claim 1 wherein the balloon further includes an elastomeric layer adjacent to the wall.

15. The balloon of claim 1 wherein the balloon further includes elastomeric material within the wall.

16. The balloon of claim 1 wherein the balloon further includes an inelastic layer adjacent to the wall.

17. The balloon of claim 1 wherein the balloon further includes inelastic material within the wall.

18. A catheter balloon, comprising a wall which is configured to retain inflation fluid in an interior of the balloon, the wall being formed at least in part of porous, expanded polytetrafluoroethylene, and at least a section of the wall being radiopaque.

19. The balloon of claim 1 further comprising a stent having a proximal end and a distal end disposed on an outer surface of the wall of the balloon.

20. The balloon of claim 19 having a proximal end and a distal end, a proximal section of balloon wall extending from the proximal end of the balloon to the proximal end of the stent, the proximal section having at least a portion that is radiopaque, and a distal section of balloon wall extending from the distal end of the stent to the distal end of the balloon, the distal section having at least a portion that is radiopaque.

21. A balloon catheter assembly for stent delivery, comprising
a) a catheter shaft having at least one lumen;
b) a polymeric balloon having a proximal skirt section and a distal skirt section sealingly secured to the catheter shaft so that an interior of the balloon is in fluid communication with the at least one lumen of the shaft and the balloon has a wall which is sealingly secured to the shaft, wherein the balloon wall has at least a section which is radiopaque, and has at least a layer formed of a porous polymeric material, and has a deflated single wall thickness of at least about 0.001 inches to about 0.0125 inches; and
c) a stent having a proximal end and a distal end disposed about the balloon.

22. A balloon catheter comprising
a) a catheter shaft having at least one lumen; and
b) a polymeric balloon comprising a wall configured to retain inflation fluid in an interior of the balloon, the wall having at least one layer formed of a porous polymeric material, at least a section of the wall having a metallic material therein.

23. The balloon of claim 1 wherein the radiopaque section has a thickness of about 0.0001 inches to about 0.012 inches.

24. The polymeric balloon of claim 22 wherein the metallic material is selected from the group consisting of barium, bismuth, tungsten, iridium, iodine, gold, iron, and platinum.

25. The polymeric balloon of claim 22 wherein the porous polymeric material is expand polytetrafluoroethylene.

26. The polymeric balloon of claim 22 wherein the balloon further includes layer formed of an elastomeric material, and the at least a section of the wall having the metallic material is at least a section of the porous polymeric layer.

* * * * *

UNITED STATES PATENT AND TRADEMARK OFFICE
CERTIFICATE OF CORRECTION

PATENT NO. : 6,652,568 B1
DATED : November 25, 2003
INVENTOR(S) : John A. Becker and Christopher C. Pfaff It is certified that error appears in the above-identified patent and that said Letters Patent is hereby corrected as shown below:

Column 3,
Line 66, delete "ad", and insert -- and --.

Column 4,
Line 24, delete "tall", and insert -- wall --.

Column 5,
Line 20, after "wall" delete "," and insert -- so that the loading percentage of radiopaque material within the polymeric wall is about 70% to about 90% by weight, --.

Column 6,
Line 3, delete "porous,".
Line 5, delete ".", and insert -- , with radiopaque material in the expanded polytetrafluoroethylene at a loading percentage of about 70% to about 90% by weight. --.
Line 31, after "and" insert -- has a loading percentage of radiopaque material which is about 70% to about 90% by weight; and --.
Line 41, delete ".", and insert -- , so that the loading percentage of metallic material in the balloon wall is about 70% to about 90%. --.
Line 49, delete "expand", and insert -- expanded --.

Signed and Sealed this

Fifth Day of July, 2005

JON W. DUDAS
*Director of the United States Patent and Trademark Office*